United States Patent [19]

Fencl et al.

[11] 4,007,088
[45] Feb. 8, 1977

[54] PROCESS OF MANUFACTURING NATIVE MICROBIAL PROTEIN WITH A LOW CONTENT OF NUCLEIC ACIDS

[75] Inventors: Zdenek Fencl; Frantisek Machek; Vladimir Sillinger, all of Prague, Czechoslovakia

[73] Assignee: Ceskoslovenska akademie ved, Prague, Czechoslovakia

[22] Filed: Aug. 8, 1975

[21] Appl. No.: 603,153

Related U.S. Application Data

[63] Continuation-in-part of Ser. No. 369,984, June 14, 1973, abandoned.

[30] Foreign Application Priority Data

June 14, 1972 Czechoslovakia .............. 4170/72

[52] U.S. Cl. .............................. 195/4; 195/28 N; 260/112 R; 426/61; 426/62; 426/429
[51] Int. Cl.² ........................................ C12D 13/06
[58] Field of Search .............. 195/2, 4, 28 N, 28 R; 260/112 R; 426/61, 62, 429

[56] References Cited

UNITED STATES PATENTS

| | | | |
|---|---|---|---|
| 3,725,075 | 4/1973 | Muroi et al. | 195/28 R |
| 3,809,776 | 5/1974 | Chao | 195/2 |
| 3,885,050 | 5/1975 | Ridgway, Jr. | 426/429 |

*Primary Examiner*—Alvin E. Tanenholtz

[57] ABSTRACT

The invention relates to a process of manufacturing native microbial protein with a low content of nucleic acids, the product being useful as food or feed. The products obtained by the process of the invention may be widely used in the food industry, especially in the meat, milk, and bread industries. These products may replace meat or milk and can also be used in the nutrition of animals. The products may also be used as substitutes for casein, in the fortification of flour, or to improve the quality and value of bread and the like.

3 Claims, No Drawings

PROCESS OF MANUFACTURING NATIVE MICROBIAL PROTEIN WITH A LOW CONTENT OF NUCLEIC ACIDS

This application is a continuation-in-part of application Ser. No. 369,984 filed June 14, 1973 and now abandoned.

BACKGROUND OF THE INVENTION

On the world market there may presently be observed a shortage of proteins, especially in the form of meat, milk, and corn, and this shortage is still increasing. For this reason, alternate sources of proteins for human nutrition are being sought. One of the proposed sources comprises the protein of single-cell microorganisms (single-cell protein) such as yeasts, bacteria, algae and the like. The advantage of the single-cell proteins consists in the possibility of automating their production, and also in the use of waste saccharides or materials of a non-agricultural origin as the starting material. The growth rate of these microorganisms is much higher than that of macroorganisms as it may be seen from Table 1, below.

TABLE 1

(according to Proces Biochem. January 1971, p.41)

| Organism | Time necessary to double the weight of cells |
| --- | --- |
| bacteria and yeasts | 20–120 minutes |
| fungi and algae | 2–6 hours |
| green plants | 1–2 weeks |
| chickens | 2–4 weeks |
| pigs | 3–5 weeks |
| cattle | 4–10 weeks |

The use of microorganisms as the source of proteins in nutrition is accompanied by some difficulties such as the usual bad smell of microorganism (e.g. yeasts), the lowered digestibility due to cell walls, the high content of nucleic acids which are deleterious to the human organism, the lowered possibility of converting the concentrate into a suitable form, lack of consistency and the like.

There are presently known procedures whereby some of these disadvantages may be eliminated. The typical yeast smell may be thus removed e.g. by extraction with a hot edible oil (Paper presented at the VIIIth Inter. Congr. of Nutrit., Prague, Aug. 28 – Sept. 5, 1969). Nucleic acids in intact cells are removed by activation of the intracellular nuclease on heating the suspension of intact cells at an elevated temperature, e.g. 75° C, for a very brief time, e.g. 15 seconds (S. B. Maul, A. J. Sinskey, and S. R. Tannenbaum in Nature 228, 181 (1970); A. Imada, A. J. Sinskey, and S. R. Tannenbaum in Biotechn. Bioengin. XIV, 103, (1972); and S. Ohta and coworkers in Applied Microbiology, Sept. 1971, (p. 415–421) the isolation of proteins from intact cells has been performed by extraction with 85% aqueous formic acid (Brit. Pat. Nos. 1,224,172; 1,224,173; and 1,224,174), with sodium carbonate (Brit. Pat. Nos. 1,234,173; and 1,234,174) or the proteins may be exracted with 8–10 molar aqueous urea for 24 hours (French Pat. No. 1,552,867).

Some preparations of the microbial protein from microorganisms consist in the mechanical disruption of cells and the subsequent extraction with sodium hydroxide at room temperature for about two hours. (Biotechnology and Bioengineering 1970, p. 947). Simultaneous extraction with neutral agents such as sodium chloride and disruption has been disclosed in Czechoslovak Pat. No. 140,926.

The disadvantage of all the known procedures based on extraction of intact cells consists in the long action of extracting agents due to the necessity of penetration of proteins through the cell wall. Since the effectiveness of extraction is very low, this process has not been so far used in industry. Industrial applications have been made possible by newer procedures which include the disruption of microorganisms, but a suitable degree of disruption may be achieved only by repeated disruptions in a homogenizer. (P. J. Hetherington in Trans. Instn. Chem. Engers. 49,142 (1971); Lars Edebo in Journal Biochem. Microbiol. Technol. Eng. 11(4),453 (1963).

SUMMARY OF THE INVENTION

The invention relates to a manufacturing process of native microbial protein with a low content of nucleic acids, the products being useful as food or feed.

The invention comprises disrupting single-cell microorganisms, the protein content of which is surrounded by the cell walls, by forming a 1% to 25% suspension of such microorganisms in an alkaline environment at pH 9–14, preferably 9–9.5, at a temperature between 0° C and 40° C, separating the cell walls at pH 7–9 from the suspension after disrupting of cell walls and precipitating the cell walls at pH 2–7 by acidification.

After disruption of cells, but prior to the precipitation of the protein, it is possible to improve the degradation of the ribonucleic acid by heating the nuclease, previously released by disruption and protected by neutralization, together with the protein to 50-60° C for 20 minutes to 2.5 hours and precipitating the protein by acidification.

The yeasts such as Candida utilis (Torula utilis) or bacteria may be used as the source of single-cell microorganisms.

DETAILED DESCRIPTION OF THE INVENTION

The process according to the present invention circumvents some of the above-described drawbacks of the earlier procedures. The process starts with a disrupted cellular material. The disruption (e.g. in glass-bead mills) is accelerated by the addition of alkaline substances (pH 9–14, preferably pH 9–9.5). Neutralization immediately follows the disruption, this eliminates the disadvantage of other procedures which include a long-termed alkaline extraction of the protein from disrupted cells and lead to a lowered content of essential amino acids, particularly lysine and methionine (the biological value of the thus-obtained protein decreases). The presence of alkali in the course of the disruption process results in a considerable decrease of the disruption time. On the other hand, the use of sodium chloride or some other extracting agents in the disruption process (cf. Czechoslovak Patent No. 140,926) does not shorten the disruption time.

The liberation of the nuclease by disruption in accordance with the invention circumvents the technologically difficult heat-shock process (cf. e.g. S. Ohta et al. above-cited) consisting in heating the Candida utilis yeast exactly for 1–3 seconds to the temperature of 68° C. Shorter periods of time are not sufficient to release the nuclease while longer periods of time lead to its inactivation. The nuclease released from disrupted cells is capable under suitable conditions, i.e. at a suitable temperature and pH value, of degrading the polymers of ribonucleic acid into nucleotides and thus preventing the precipitation of the former during the isolation of proteins.

In accordance with the process of the invention, cell walls are removed before or after the degradation of ribonucleic acids. Such cell wall removal is accomplished by centrifugation or filtration. The protein which is dissolved in the supernatant or filtrate is precipitated by adjusting the pH value to the isoelectric point. The precipitation may also be accomplished by the addition of enzymatical preparations obtained either from stomach juices of mammals or prepared by a microbial route (cf. precipitation of milk protein). The precipitation effect is increased by the addition of bivalent cations such as $Ca^{++}$ which simultaneously enrich the protein with calcium. The protein precipitate is separated from the liquid phase either by filtration or on the basis of the different specific weights. The liquid phase which contains fragments of nucleic acids, amino acids, peptides and growth substances, is concentrated and the concentrate is dried together with the cell walls for use as feed, or processed separately from the cell walls and used as the source of flavor or aromatic substances in the food industry, as the source of amino acids or nucleosides, or as a vitamin concentrate. The isolated protein is cautiously dried. Components of the lipoid character are extracted either directly from disrupted cells (especially in the case of microorganisms cultivated on hydrocarbons) or from the protein concentrate (moist or dry) with alcohol.

When a dry protein concentrate is extracted, the final protein retains a higher proportion of native proteins. In the recovery of the solvent, a fat is obtained which may be used, according to the origin of the microorganism, either in the food industry or as a technical fat. After the extraction step, the protein concentrate is dried to remove the traces of the solvent. The protein concentrate may also be used as an ingredient of foods as a substitute for animal protein, in the fortification of starch foods (bread and the like) or to simulate the texture of meat and meat products. In contrast to the protein within the cells, the dried protein concentrate according to the present invention exhibits higher digestibility and a higher biological value.

Table 2 below shows the biological value of various proteins in comparison with that of proteins from Candida utilis obtained according to the process of the invention (dried protein concentrate):

TABLE 2

Biological Values of Various Proteins

| Protein | average of reported biological values | |
|---|---|---|
| gelatine | 5.87 | |
| wheat glutein | 60.00 | |
| wheat gluten | 55.32 | |
| peas | 61.20 | |
| casein | 70.40 | |
| soya | 72.20 | |
| beef and veal | 78.20 | |
| poultry | 74.00 | |
| pork | 74.00 | |
| fish flour | 84.90 | |
| egg albumin | 83.00 | |
| eggs | 95.74 | |
| Saccharomyces cerevisiae (dried) | 61.50 | |
| Candida utilis (dried) | 31.80 | (acc. to Food and Agriculture Org.) |
| " | 67.70 | (nonstandard analyses) |
| dried protein concentrate obtained according to the invention from Candida utilis | 72.93 | |

The invention is illustrated by the following Examples.

EXAMPLE 1

The RNA level in the yeast cell homogenisate was lowered by activation of its own yeast nuclease as follows: Thus, 1000 g of the disrupted yeast suspension of Saccharomyces cerevisiae (prepared in a glass-bead mill and containing 93 g of the yeast dry matter and 8.1 g of nucleic acids) was adjusted to pH 5.9 with hydrochloric acid and was maintained under constant stirring for one hour at a temperature of 53°C. The suspension was then cooled down with tap water and the protein was precipitated. By the action of nuclease, the content of nucleic acids was lowered to the value of 0.85 g.

EXAMPLE 2

Nucleic acids of the disrupted bacterial suspension of Escherichia coli were degraded as follows. Thus, 100 ml of the disrupted 5% E.coli suspension was adjusted to pH 8.0, diluted with 400 ml of a 0.1 M phosphate buffer solution, heated to 60°C, and maintained at this temperature for 1 hour. After the incubation, a 1-ml sample was withdrawn and the RNA was determined in this sample. The sample contained 16 microgram per 1 ml of nucleic acids (the original amount of nucleic acids was 54 microgram per 1 ml). The content of nucleic acids was thus lowered by about 70%. In each of examples 4 and 5 all percentages are by weight.

EXAMPLE 3

The process of each of Examples 1–4 inclusive was repeated except for the use of yeasts of the genus (1) Torulopsis, (2) Rhodotorula, (3) Oiidium, (4) Pichia and (5) Hansenula.

EXAMPLE 4

The process of Example 5 was repeated except for the use of bacteria of the genus (1) Megaterium, (2) Methanomonas, and (3) Pseudomonas.

The dry protein powder obtained by the practise of the present invention has a low content of nucleic acids (less than 1%), is tasteless, in color is white to weakly tan, and may be stored for a longer period of time than those produced in accordance with prior art processes. The protein powder made in accordance with the invention may be used in food industry, especially in the meat, milk and bread industries; thus it may be used in meat products, artificial milk, particularly in the nutrition of animals, as a substitute of casein, in the fortification of flour and in improving the quality and nutritive value of bread.

Although the invention is illustrated and described with reference to a plurality of preferred embodiments thereof, it is to be expressly understood that it is in no way limited to the disclosure of such a plurality of preferred embodiments, but is capable of numerous modifications within the scope of the appended claims.

What is claimed is:

1. A process for producing native microbial protein from single-cell microbial cells having a content of nucleic acids lower than 1% and useful as food or feed, which comprises the steps of:
    a. disrupting microbial cells to release the nuclease contained therein and forming thereafter a homogenate having disrupted cells and nuclease;
    b. adjusting the pH value of the said homogenate to 5.9–8.0 and maintaining the temperature at 50°–60°C for 20 minutes–2.5 hours in order to permit the degradation of nucleic acids by means of the nucleases contained in the homogenate;
    c. precipitating protein material from the microbial homogenate by adjusting the pH value to the isoelectric point of the protein material;
    d. separating the precipitated protein material;
    e. drying the precipitated protein material;
    f. extracting the precipitated and dried protein material with alcohol to remove lipoid substances; and
    g. drying again said extracted protein material.

2. Process in accordance with claim 1, wherein the subject single-cell microbial cells are chosen from the group of yeasts consisting of the genus *Saccharomyces cerevisiae*, *Candida*, *Torulopsis*, *Rhodotorula*, *Oiidium*, *Pichia*, and *Hansenula*.

3. Process in accordance with claim 1, wherein the single-cell microbial cells are chosen from the group consisting of bacteria of the genus Megaterium, Methanomonas, and *Escherichia coli*.

* * * * *